United States Patent [19]

Woodrow et al.

[11] 4,165,939
[45] Aug. 28, 1979

[54] APPARATUS FOR INSPECTION AND DIMENSIONAL MEASUREMENT BY SEQUENTIAL READING

[75] Inventors: Arthur F. Woodrow; Jorge E. Simmons, both of Tucson, Ariz.

[73] Assignee: TSN Company, Inc., Tucson, Ariz.

[21] Appl. No.: 735,844

[22] Filed: Oct. 26, 1976

Related U.S. Application Data

[63] Continuation-in-part of Ser. No. 543,063, Jan. 22, 1975.

[51] Int. Cl.² .................. G01B 11/24; G01N 21/32
[52] U.S. Cl. .................. 356/394; 250/223 R; 250/572; 356/237
[58] Field of Search ............... 356/120, 164, 165, 167, 356/168, 200, 209, 237; 250/562, 563, 572, 224, 223 R, 223 B

[56] References Cited

U.S. PATENT DOCUMENTS

| | | | |
|---|---|---|---|
| 3,131,815 | 5/1964 | Mathias | 356/209 |
| 3,529,169 | 9/1970 | Heaney et al. | 250/223 B |
| 3,536,899 | 10/1970 | Gebel | 250/211 R |
| 3,749,496 | 7/1973 | Hietanen et al. | 356/167 |
| 3,794,427 | 2/1974 | Shibata et al. | 356/120 |

*Primary Examiner*—Vincent P. McGraw
*Attorney, Agent, or Firm*—Cahill, Sutton & Thomas

[57] ABSTRACT

An inspection system is disclosed for detecting dimensional tolerances, shape and cosmetic defects in containers. A conveyer carries the containers past an inspection point where at least one focused beam of radiant energy traverses the container's surface at a steep angle. The pattern of the surface is detected and evaluated by optical imaging techniques to determine the acceptability of the inspected container while maintaining a capability of making allowances for manufacturing tolerances of the relative position of the area under inspection with respect to a given reference point of the container. Means are also disclosed for initiating and terminating the inspection process dependent upon the translational position of the container with respect to the inspection system.

16 Claims, 19 Drawing Figures

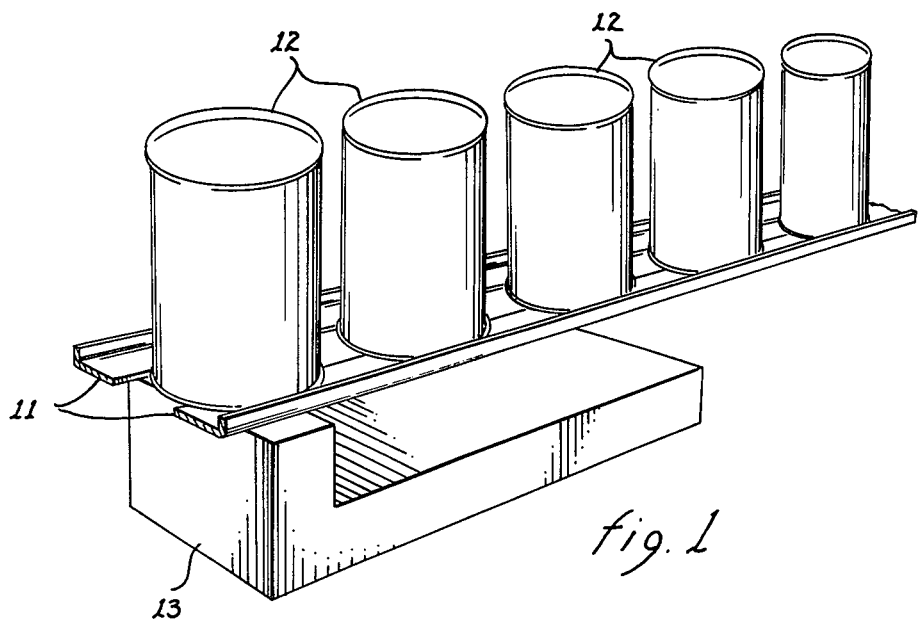
fig. 1
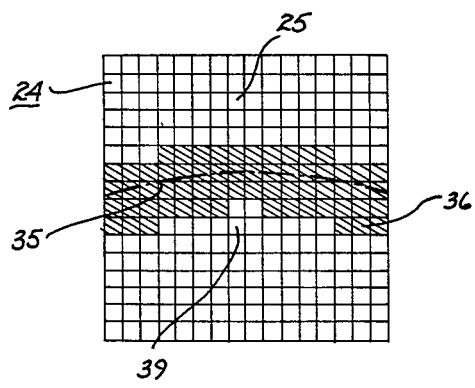
fig. 4
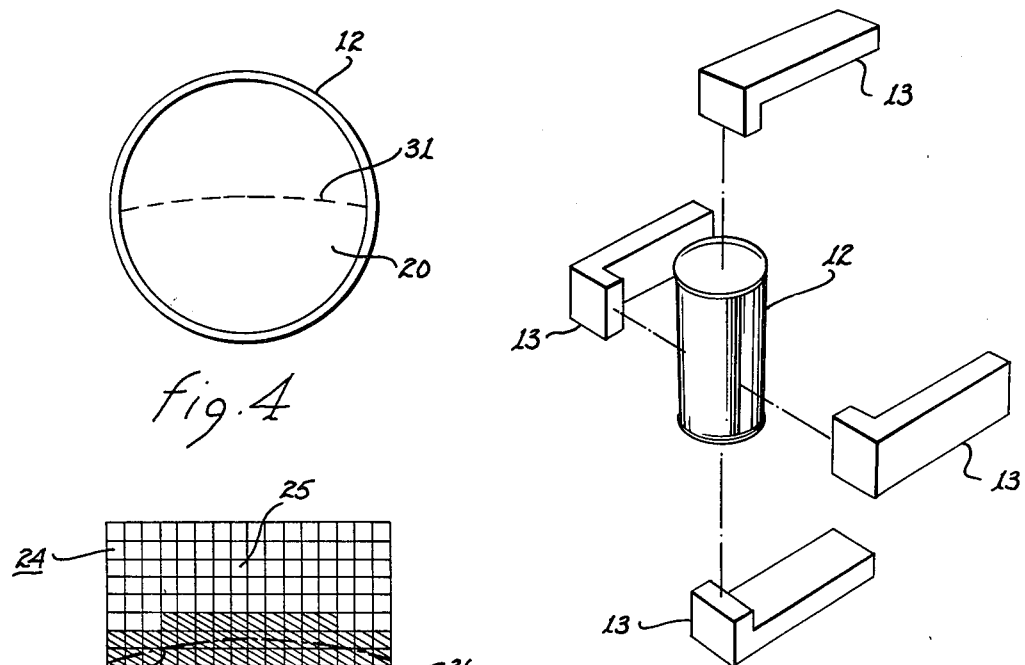
fig. 5
fig. 2

APPARATUS FOR INSPECTION AND DIMENSIONAL MEASUREMENT BY SEQUENTIAL READING

RELATED INVENTIONS

The present application is a continuation-in-part application of an application entitled "Inspection System for Container Integrity", filed Jan. 22, 1975, assigned Ser. No. 543,063, and describing an invention made by the present inventors and assigned to the present assignee.

FIELD OF THE INVENTION

This invention relates to inspection equipment and, more particularly, to equipment adapted for detecting dimensional tolerances, shape and cosmetic defects in containers.

BACKGROUND OF THE INVENTION

In present day canning factories, conveyer speeds in excess of one thousand units per minute are not unusual. Not only do the high operating speeds cause occasional damage to the containers as they move along the conveyer, but the high speed also makes inspection for any damaged units extremely difficult. In U.S. Pat. No. 3,131,815, issued May 5, 1964 to B. B. Mathias, method and apparatus are disclosed for inspecting sealed containers by detecting a light beam reflected from a surface of the container. If the surface under inspection is of a predetermined configuration, the reflected light is focused upon a first detector. Should the surface be deformed, some light will be reflected through one or more laterally located lenses to impinge upon a second detector. Energization of the second detector generates a signal to identify the defective container. William T. Plummer et al., in U.S. Pat. No. 3,761,179, issued Sept. 25, 1973, discloses apparatus for testing a mirrored surface by detecting the light reflected from the surface. Inspections which rely on reflected light are adversely affected by the presence of dirt, foreign matter or overflow from the containers. Because foreign material cannot be completely avoided in a canning factory, inspection systems of the Plummer type will unnecessarily reject a container merely because the inspected surface is dirty; similarly, diffused surfaces will generate error signals falsely indicative of damaged or deformed containers.

It is therefore an object of our invention to inspect containers without regard to the specular reflective characteristics of the tested containers.

The testing disclosed by the Mathias apparatus is effective only after a container has been filled and sealed since the presence of a vacuum within the container is required. No provision is made for detecting defective containers prior to the filling and sealing operations. As a result, every container, whether defective or not, must be filled and sealed prior to being inspected. Any material used to fill a defective container is wasted. If defective containers were identified prior to the filling and sealing operation, contents could be saved that would otherwise be wasted by filling defective containers.

It is therefore also an object of our invention to inspect containers prior to the filling thereof to determine the presence of defects in the containers.

The patent to Shibata et al., U.S. Pat. No. 3,794,427, issued Feb. 26, 1974, describes apparatus which employs the principles of light reflection (angle of incidence equals angle of reflection) to detect conformity of a surface under inspection with a predetermined norm. A television camera scans or views the reflection received from an illuminated object traveling in a direction transverse to the source of light. The amplitude of the signal generated by the television camera during the scan is correlated with respect to a time base and compared with the amplitude per time base of a norm. An output signal responsive to the comparison step is generated to provide an indication of conformity with the norm of the object under inspection.

Another object of the present invention is to provide an inspection system wherein the detector system does not scan the surface under inspection.

Still another object of the present invention is to provide an inspection system wherein a light source and light detection system are not necessarily transverse to and at opposed sides of the object under inspection.

Dimensional inspection of objects can be accomplished optically. In U.S. Pat. No. 3,536,405, issued Oct. 27, 1970, to R. A. Flower, a system for inspecting the thickness of a sample is disclosed. Similarly, L. F. Flaczynski in U.S. Pat. No. 3,682,554, issued Aug. 8, 1974, discloses a method and apparatus for dimensionally inspecting conveyer goods while they move along the conveyer. The patent to Hietanen et al., U.S. Pat. No. 3,749,496, issued July 31, 1973, describes an inspection system employing a laser. The intensity of the lased surface, on comparison with a norm, provides an indication of the degree of conformity of the object under inspection. Size gauging method and apparatus are disclosed in U.S. Pat. No. 3,791,741, issued Feb. 12, 1974, to I. R. Brenholdt. Each of the above cited references is capable of optically inspecting a sample to determine its dimensional characteristics within a given tolerance. However, the apparatus disclosed in each of the references would be unable to detect a defect in a container shape unless that defect appeared in the specific surface being inspected and affected its size. For example, a can which had a hole in the middle of the inspected surface could pass a height and width dimensional inspection because the hole would not alter the external dimensions of the surface. However, such a defective can should be detected by a sophisticated inspection system to prevent a wasteful filling operation.

It is another object of our invention to inspect container goods simultaneously for dimensional variation and non-dimensional defects.

R. A. Webster in U.S. Pat. No. 3,222,979, issued Dec. 14, 1965, discloses an electron-optics device for dimensionally inspecting objects. The device employs a scanning electron beam to inspect the object. The electron scan is converted into a video output for determing the acceptability of the inspected object. The scanning beam is a movable source, returning periodically to some starting point for initiating the scan of a subsequent object. Because of the time required to scan a sample, such device could not be effectively employed in a conveyer system operating at the speeds previously indicated.

It is yet another object of our invention to employ a fixed position beam to inspect containers.

U.S. Pat. No. 3,619,578 which issued Sept. 22, 1969, to P. George and U.S. Pat. No. 3,695,771, which issued Oct. 3, 1972 to A. M. Bardos, disclose inspection equipment for detecting surface irregularities on inspected samples. Both disclosed patents are limited to determining defects in surface smoothness.

It is one of the objects of our invention to simultaneously inspect a container for dimensional conformity and surface acceptability.

All the inspection systems discussed above have been effective for inspecting a single surface of a sample. However, a container may have defects on any of its surfaces which require rejection of the container. Because the above systems cannot interpret the effect a defect in one surface has on other surfaces of a container, defects on surfaces other than the inspected surface would not be detected.

It is still another object of our invention to permit simultaneous testing of any or all surfaces of a container for the presence of defects.

An additional object of our invention is to permit the detection of defects in any surface of a container by inspecting a portion of a single surface of the container.

A further object of the present invention is to employ a gating system for initiating and terminating the inspection process.

A still further object of the present invention is to correlate the translational position of the object under inspection with the simultaneous information acquired by the inspection system.

A yet further object of the present invention is to gate an inspection system independent of the translational speed of the object under inspection.

SUMMARY OF THE INVENTION

The present invention employs the technique or principle of optical imaging wherein it is inconsequential whether the angle of incidence of a beam of light impinging upon the surface under inspection is equal to the angle defined by the surface under inspection and a line extending from an illuminated point on the surface to an energized detector. The surface to be inspected is brightly illuminated at a steep angle of incidence by a point source or a predetermined light pattern impinging upon the surface under inspection. The surface under inspection may be reflective, granular, or diffused. An energized detector or a bank of energized detectors sense whether the illuminated surface (light pattern developed on the surface under inspection) is of a predetermined configuration. If it is not, a signal representative of a defective inspected surface and, hence, a defective object is generated. By using optical imaging techniques rather than detectors dependent upon a predetermined reflection angle, the specular reflecting properties of the surface under consideration are incidental and the surface under inspection may be diffused, granular, etc.

BRIEF DESCRIPTION OF THE DRAWINGS

FIG. 1 is a perspective view of an inspection system embodying our invention;

FIG. 2 is an exploded perspective view of a system embodying our invention and adapted for simultaneously inspecting all surfaces of a container;

FIG. 4 is a plan view of a can end undergoing inspection in accordance with our invention;

FIG. 5 is a plan view of the detector array shown in FIG. 4;

DETAILED DESCRIPTION OF THE ILLUSTRATIVE EMBODIMENT

Figure 3:
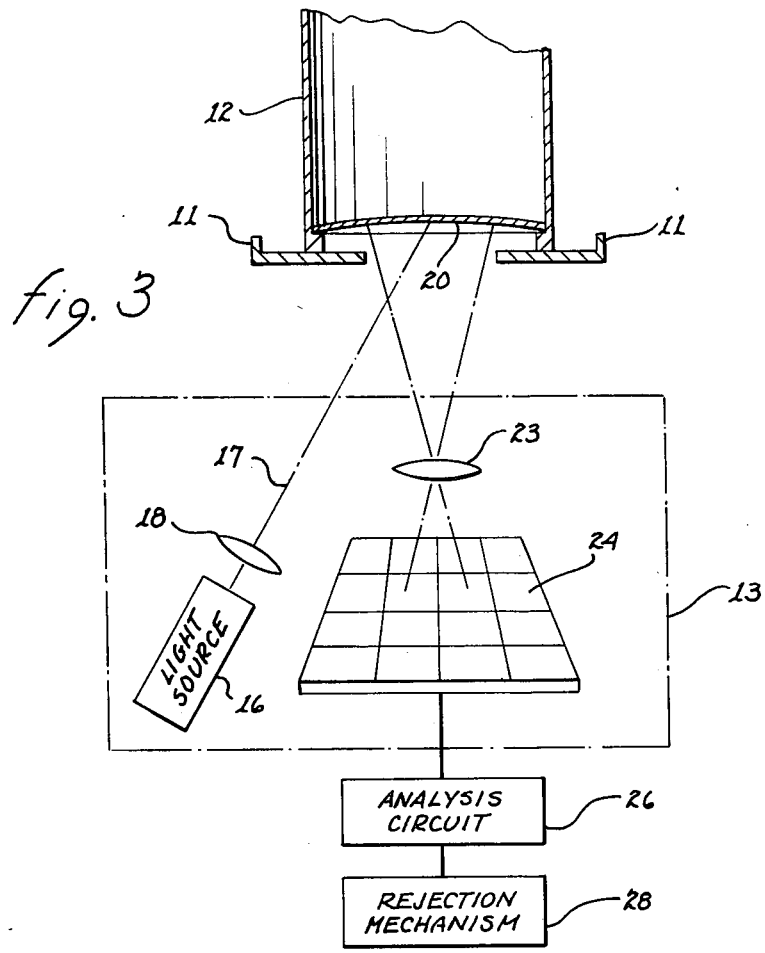
FIG. 3 is a diagramatic representation of the system shown in FIG. 1.

A can moving conveyer 11 is shown in perspective in FIG. 1. Conveyer 11 transports a plurality of cans 12 past a monitoring station 13 to inspect the cans for defects. A beam of high intensity light, such as a laser, is positioned to impinge upon the bottom surface of cans 12 as the cans pass monitoring station 13. The beam, which may define a cross-sectional pattern such as a point source, a two dimensional array or an array of points, impinges on a can bottom at a steep angle. The steep angle in combination with the intensity of the beam results in an illuminated area or image upon the bottom of the can commensurate with the pattern of the beam and the surface configuration of the can bottom. For the type of objects to be inspected, such as can bottoms, the surface to be inspected is not normally specularly optically smooth and scattering of light will occur. A part of the light scattered by the image developed upon the can bottom is focused by lens 23 on detector array 24 (see FIG. 3). Ultimately, the energized detectors of the detector array and attendant circuitry will provide an indication of the size and shape of the illuminated image, hence the configuration of the can bottom. From the above, it becomes apparent that the detectors or monitoring apparatus need not be at the exit pupil of the optical system as would be true were the surface to be inspected too specularly smooth to produce scattering. Accordingly, this system obviates the need for video scanners or the high alignment accuracy requirements of inspection systems dependent upon specularly smooth surfaces and equal angles of incidence and reflection.

For reasons which will be explained later, the inspection of only the bottom surface of can 12 will permit the detection of defects in any of the surfaces of can 12. However, in particular applications or where it is desired to produce redundant outputs or where an extreme degree of reliability is required, more than a single surface of can 12 can be inspected by segregated inspection systems. For example, the exploded perspective view of FIG. 2 shows a can 12 at the center of four monitoring stations 13. These stations can simultaneously inspect the can top and bottom as well as opposite sides, effectively inspecting all surfaces of the can.

As shown in the cross-sectional view of FIG. 3, conveyer 11 has an open bottom to permit the illuminating beam to impinge directly upon can 12. Monitoring station 13 includes a source 16, such as a laser, which produces the high intensity illuminating beam. The input ray 17 of the beam is focused by lens 18 along a fixed axis to sweep across the normally concave bottom 20 as can 12 is transported along conveyer 11. Because bottom 20 is concave and ray 17 is focused along a fixed axis, the ray will not sweep across the bottom of can 12 in a straight line as the can moves past the ray. A curved track 31, as shown in FIG. 4, will result since ray 17 will have to travel farther to impinge on the center of bottom 20 than it will at the edge. The light emanating from the illuminated image will be focused by lens 23 onto detector array 24, as shown in FIG. 3.

Detector array 24 includes a plurality of detector elements (detectors) 25 arranged in a grid-like configuration as shown in FIG. 5. The curvature of can bottom 20 at the points along which input rays 17 impinge in combination with lens 23 will determine which detectors of detector array 24 will be energized. The number and sequence of energized detectors will correspond to the bottom 20 which is impinged by the inspecting beam.

In order to accommodate normal tolerances, inspected cans that vary only slightly from the ideal or standard must be distinguished from those with more significant defects. The ideal track 35 of energized detectors, shown dotted across array 24 in FIG. 5, would be produced by inspecting an ideal or standard can. An "envelope" 36 of detectors 25 (shown shaded in FIG. 5) delineates the area in which the track of an inspected can must fall to be within the limits of acceptable variation from the ideal or standard. Should the track of an inspected can fall on a detector located outside envelope 36, such as detector 39, the inspected can would be rejected.

Detector array 24 provides an input signal to an analysis circuit 26. The location of all detectors corresponding to envelope 36 are programmed into analysis circuit 26. Should the inspection beam produce a track that is detected by another detector, analysis circuit 26 would determine that a defect was present of such magnitude as to cause deviation from the ideal or standard to an unacceptable degree. A rejection mechanism 28 would be actuated to either remove the rejected can from the conveyer or identify the rejected can for subsequent removal.

Detectors 25 of detector array 24 may be made capable of detecting not only the presence or absence of light, but also the amplitude of the light received. In combination with analysis circuit 26, detector array 24 may also determine the rate of change in amplitude of light from a moving light track. Monitoring these criteria and comparing them with predetermined standards, permits a variety of features of an inspected can to be evaluated. In addition to size and shape characteristics, certain cosmetic features of a can may be determined as well. For example, it may be desirable to monitor the placement or color suitability of advertising indicia on the surface of a can or carton. Monitoring the rate of change in amplitude of the reflected light will provide an indication of any variation in texture, color or any other irradiance property of the inspected surface. This inspection may be done concurrently with the shape inspection previously described.

Although all surfaces of a can 12 can be monitored simultaneously, this would be unnecessary for most applications. Because alterations in any surface of a can will produce a corresponding change in the configuration of the other surfaces of the can, monitoring a single surface will normally detect defects in any surface. As an example, if the side of a can were dented, at least one edge of the bottom surface would be drawn toward the dent by at least a few microns. By monitoring only the bottom surface of a can using a sensitive detector array, an alteration in other surfaces of the can besides that of the bottom would produce a detectable change in the image received at the detector array. In general, the bottom surface would be monitored for a container since that is most sensitive to defects which may occur on other surfaces.

There are situations in which particular aspects of other surfaces of the container need to be monitored. One example would be the inspection of the side surfaces of a barrel or drum. Drums contain a plurality of convolutions or circumferential ribs around several positions on their side surface. These ribs provide resiliently compressible annular regions to prevent the buckling of the drum side when the drum is placed under end to end loads. The placement and shape of the compressible ribs is relatively critical and the need for monitoring is apparent.

Because the output of detector array 24 is analyzed by analysis circuit 26 and compared to a programmed acceptable pattern, it is possible to check only particular points on an inspected surface. This process is analogous to a masking process in which the light detection from only particular points is given significance. This masking process could be used advantageously in inspecting the top of snap-tab cans to determine the acceptability of the placement and orientation of the tabs. An additional example would be a can bottom that has multiple regions on its surface. Such multiple regions result where a closeable opening is positioned within the general bottom surface.

Figure 6:
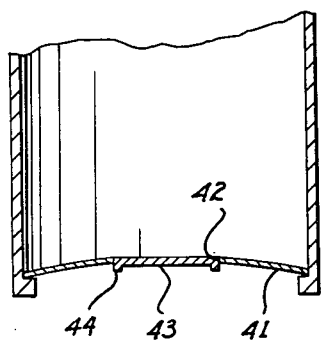
FIG. 6 is a cross-sectional view of a can having a closure in an end thereof.
Figure 7:
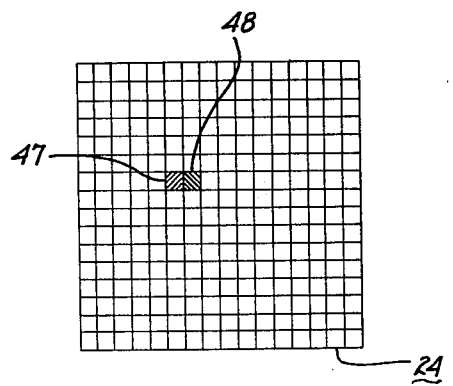
FIG. 7 is a plan view of the detector array shown in FIG. 4.

FIG. 6 shows a cross-sectional view of such a can. The multi-regioned bottom 41 includes an opening 42. A closure 43 is friction-locked into opening 42 by an edge rib 44. To determine the proper positioning of closure 43, the entire surface of the container need not be inspected. Merely checking a point on bottom 41 contiguous to rib 44 and checking a point contiguous to the rib on closure 43 will be sufficient to show the relative position of the bottom and the closure. If the image of the inspecting light beam is detected by masked detectors 47 and 48, as shown in FIG. 7, corresponding to the two points contiguous to rib 44, the inspected can is acceptable. If the illuminated portion of the image falls on other detectors of detector array 24, the rejection mechanism 28 is actuated as previously discussed.

The manufacture of two piece aluminum and steel cans involves drawing and ironing the can from flat stock. Maximum stress and deformation occurs at the juncture between the bottom and the sides. Due to the deformation, particularly at the juncture, voids may form which result in air leaks. Steel cans and drums are manufactured by welding formed sheet stock. Air leaks may occur along seam lines similar to those occurring in aluminum and steel cans. Even if the air leak is so small that contents won't be lost, the leak would provide entree for bacteria. In order to determine the integrity of a formed unit, a temporary vacuum is applied. The presence of a partial vacuum at the interior of an airtight can will produce a detectable inward movement of the outer surfaces of the unit. If any air leak is present, the inward movement would not occur, because a vacuum could not be formed.

It should be pointed out that light source 16 is representational only. Any source of radiant energy, or a plurality of sources, could be used so long as a corresponding change is made in the detectors of the detector array. In addition, although detector array 24 was depicted as a 16×16 arrangement of detectors 25, any number or arrangement could be used. Where the necessity for extreme sensitivity exists and the economics warrants the increased expense, many more small sized detectors could be used. The converse, less units, could also be used where less sensitivity is required. Nor must the array of detectors be square. They may be arranged in any position, along either side of track 35 for example, that the particular application would effectively utilize.

Figure 8A:
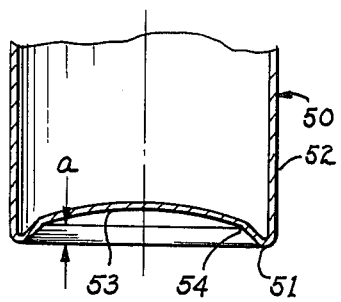
FIGS. 8a, 8b and 8c depict various cross-sections of beverage cans.
Figure 8B:
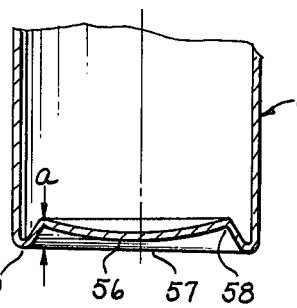
Figure 8C:
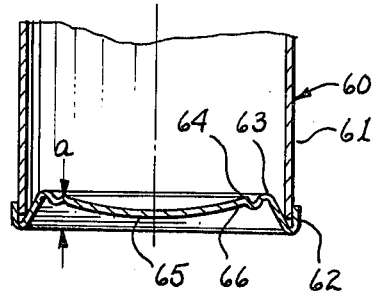

Beverage cans, whether made of aluminum or tin stock, generally have the bottom surfaces of the cans counter sunk from the lower circumferential edge. FIGS. 8a, 8b and 8c illustrate cross-sections of representative cans. FIG. 8a depicts a can 50 having its cylindrical wall integrally formed with the bottom surface. A circular ridge 51 is disposed at the lower periphery of side wall 52 and extends inwardly and upwardly to annular junction 54 of concave surface 53 defining the major area of the bottom of the can. The concave curvature of bottom 53 is predetermined such that any change in curvature would represent deformation of a surface portion of the can or indicate substantial over or under pressurization of the contents within the can. FIG. 8b represents a can 55 similar to that of can 50 but having a flattened central circular area 57 surrounded by a convex bottom 56 extending from annular junction 58 at the upper inward wall of circular ridge 59. FIG. 8c depicts a can 60 having a cylindrical side wall 61 and an attached bottom cap 62. The cap includes a plurality of annular ridges 63 and 64 defining a convoluted surface with a circumscribed convex circular area 65 extending inwardly from annular junction 66. The distance depicted in FIGS. 8a, 8b and 8c by the lower case "a" defines the degree of counter sink of the bottom surface and is identified as the distance between the bottom of the respective can ridge and the annular junction intermediate the circumscribed circular concave or convex bottom area.

Figure 9:
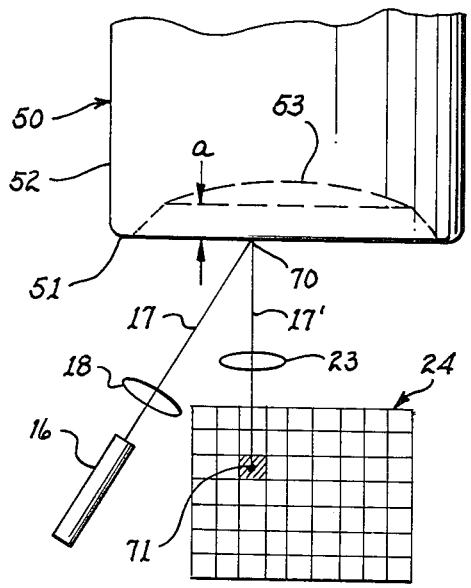
FIG. 9 is a diagramatic representation of step one of the inspection process.

During manufacture of beverage cans, it is economically unfeasible to maintain distance "a" to tolerances of much less than ten thousandths of an inch; were the tolerances maintained much closer, the expense of manufacture would be increased substantially. Consequently, the height of the concave or convex circular bottom area above the plane defined by the circumferential ridge of the can will vary from can to can even though the curvature of this bottom area will remain constant from can to can. The apparatus to be described correctly and accurately compensates for these differences resulting from the manufacturing process without jeopardizing the integrity of the curvature inspection and detection aspects of the invention. Turning now to FIG. 9, there is illustrated a schematic diagram of a can, such as can 50 illustrated in FIG. 8a undergoing initial inspection. A high intensity beam of light 17 is emitted from light source 16 through a lens system 18 to project an illuminated pattern or image 70 at the bottom of ridge 51 of the can. For purposes of illustration, it is assumed that the path of the can is toward the viewer and that the image is at the leading edge of the ridge. The light emanating from image 70 and depicted by path 17', is acted upon by lens system 23 to energize detector 71 of detector array 24. For reasons which will become apparent below, energization of detector 71 serves as a reference to which the subsequently energized detectors are compared to compensate for the counter sink distance "a", which may vary. Thereby, despite variation of the counter sink, accurate inspection of the bottom area is not jeopardized.

Figure 10:
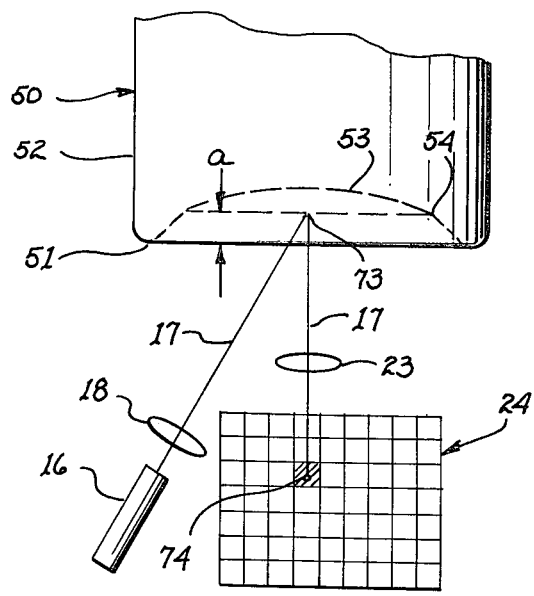
FIG. 10 is a diagramatic representation of step two of the inspection process.

Upon translation of can 50 toward the viewer, as shown in FIG. 10, high intensity beam 17 emanating from light source 16 through lens system 18 will impinge upon and create an illuminated area 73 at annular junction 54 intermediate the periphery of bottom area 53 and the upper edge of the inner surface forming ridge 51. Because illuminated image 73 is laterally displaced from illuminated image 70 (see FIG. 9), the light emanating from illuminated image 73 along path 17' will be acted upon by lens system 23 to energize a detector 74, which detector is positionally displaced from detector 71. As stated above, the manufacturing tolerances of the counter sink, represented by "a" is expected to vary by a certain degree. This variation is reflected upon detector array 24 by displacement between detectors 71 and 73. The displacement of the energized detectors, if intermediate a detector within a first envelope of detectors and a detector within a second envelope of detectors, the counter sink is determined to be within a predetermined tolerance and inspection of the contour of bottom area 53 will continue. Should either detector 71 or 74 be outside of either of two predetermined envelopes, a reject mechanism could be actuated to mark and/or otherwise identify the can under inspection for rejection. Alternatively, the inspection of the curvature of bottom area 53 could be allowed to proceed, depending upon the program established within the analysis circuitry attendant the apparatus. As a yet further alternative, energization of detector 71 could be employed to serve as a datum for a height measurement of the trace effected upon total bottom area 53 of can 50 and appropriate circuitry would be employed to subtract the height represented by detector 74 with respect to the height represented by detector 71 so as to give a height profile of bottom area 53. Whichever type of analysis circuitry is employed, the determination of whether or not can 50 passes inspection is primarily dependent upon the number and sequence of detectors energized by the light emanating from the series of illuminated images or illuminated trace across the bottom surface of the can.

Figure 11:
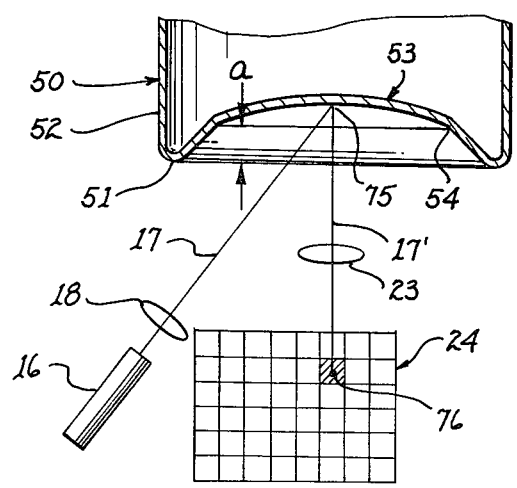
FIG. 11 is a diagramatic representation of step three of the inspection process.

FIG. 11 is similar to FIG. 10 except that can 50 has been translated or positioned toward the viewer such that beam 17 impinges upon and creates an illuminated image 75 upon bottom area 53. A part of the light emanating from illuminated image 75 is directed along path 17' through lens system 23. Because illuminated image 75 is laterally displaced from illuminated image 73 (see FIG. 10), lens system 23 will cause the light emanating from illuminated image 75 to impinge upon detector 76, which detector is positionally displaced from detector 74 (see FIG. 10). Further translation of the beam across bottom area 53, occurring due to movement of the can, will energize further detectors as described above with respect to FIGS. 3, 4 and 5.

Figure 12:
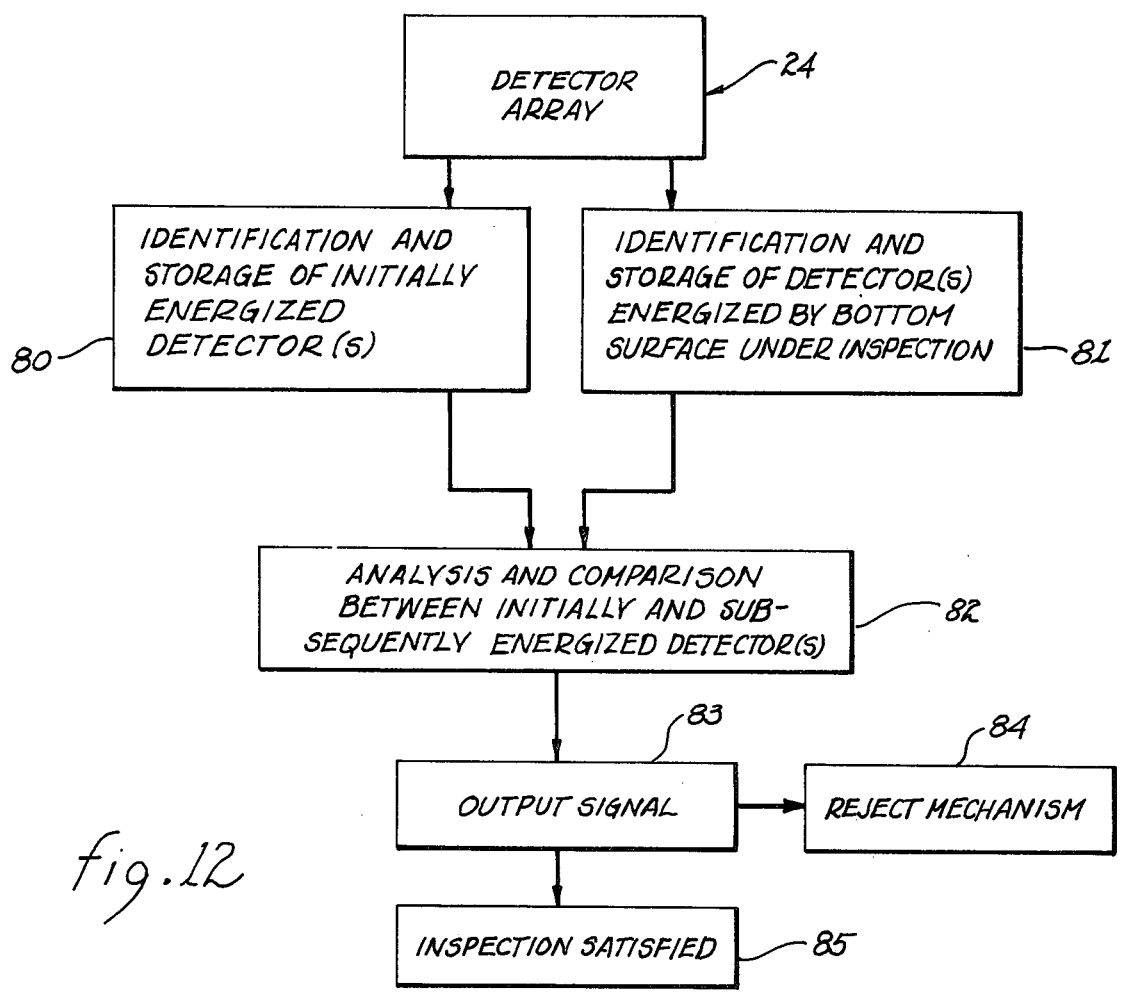
FIG. 12 is a block diagram of the associated electronic system.

A representative block diagram of the attendant circuitry is illustrated in FIG. 12. The detector within detector array 24 initially energized by the illuminated image upon ridge 51 is identified and stored within block 80. The subsequent detectors energized are identified and stored within block 81. The stored information is retrieved and transmitted to an analysis and comparison circuitry identified by block 82. Therein, a determination is made of whether bottom area 53 is of an appropriate curvature with due regard to the degree of counter sink. An output signal 83 from block 82 either energizes a reject mechanism 84 or provides an indication of satisfactory inspection as depicted in block 85. For the sake of economy, the circuitry attendant block 85 may be deleted whereby no manifestation of satisfactory inspection occurs and only those cans producing a failure mode situation cause a further signal to be generated.

FIGS. 13, 14a, 14b, 14c and 14d depict a timing or sequencing sensor system for gating the information provided by detector array 24. Conveyer 11, in the manner indicated in FIG. 3, conveys the objects or cans to be inspected from left to right as indicated by the arrow. Light source 16 radiates a high intensity light beam 17 through lens system 18 to intercept and impinge upon the cans translating therepast. A sensor system, having pairs of transmitters and receivers 90a, 90b, 91a, 91b, 92a, 92b and 93a, 93b, respectively, intercept the leading edge of the can as it passes therepast. Upon interception, a signal is generated by the respective one of the receivers and is conveyed to either the identification and storage system (blocks 80 and 81 as shown in FIG. 12) or to the analysis and comparison circuitry (block 82 as shown in FIG. 12) to identify or otherwise code the signal emanating from the presently energized one of the detectors within detector array 24.

Figure 13:
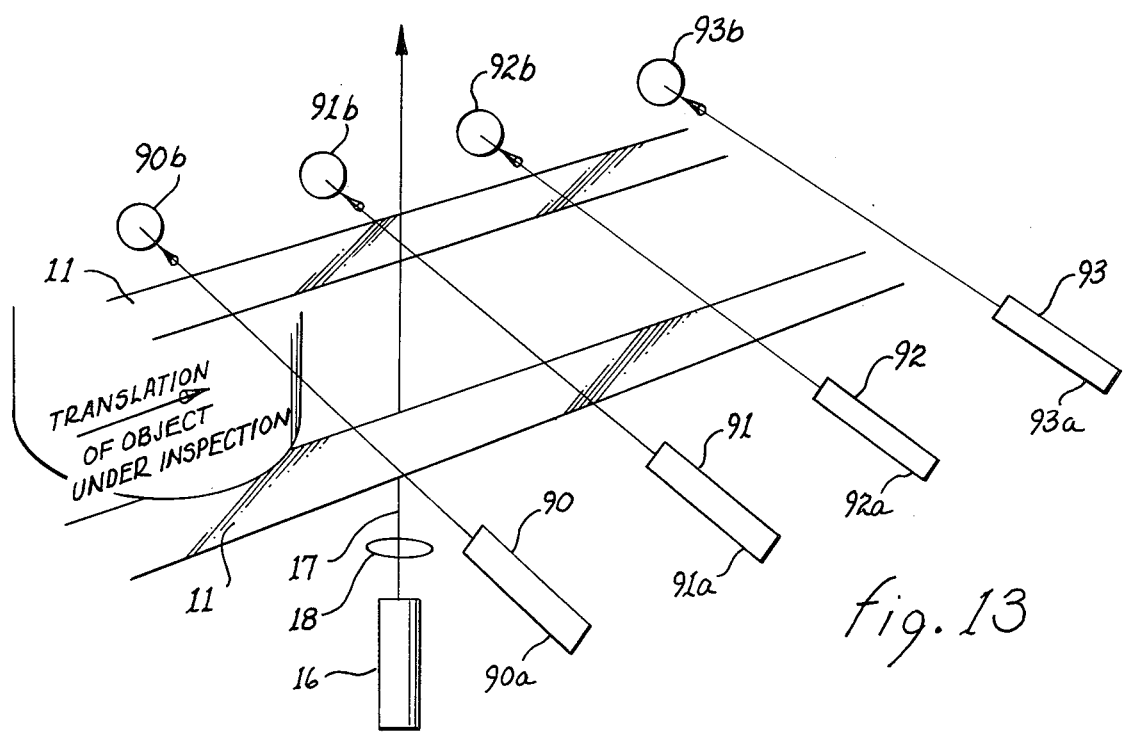
FIG. 13 is a diagramatic representation of the gating system.
Figure 14A:
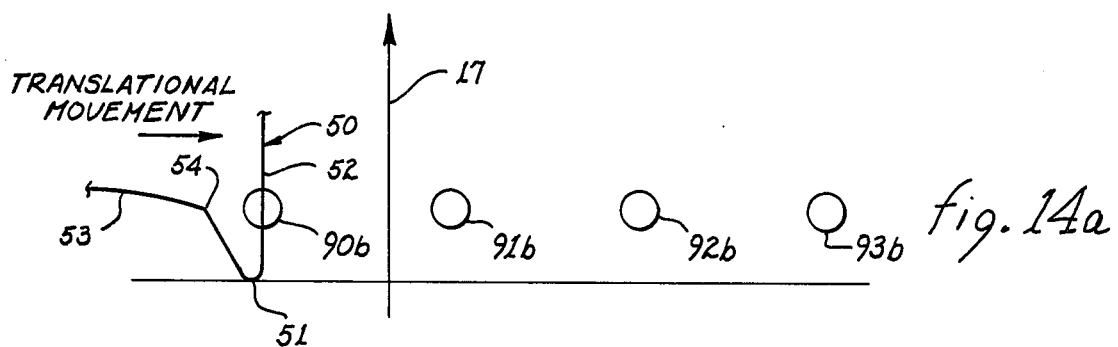
FIGS. 14a, 14b, 14c and 14d illustrate operative steps of the gating system.
Figure 14B:
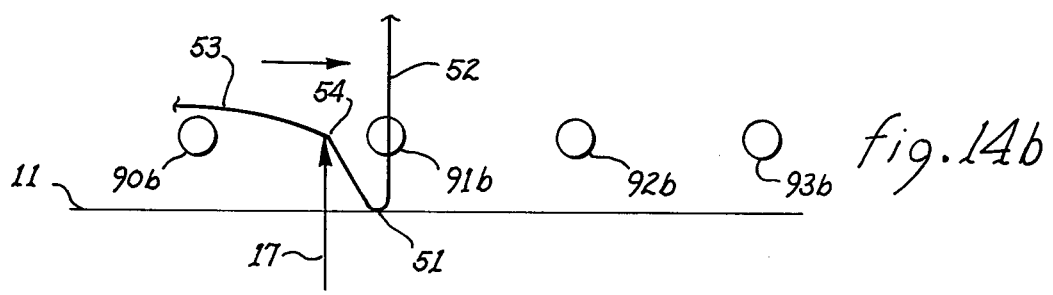
Figure 14C:
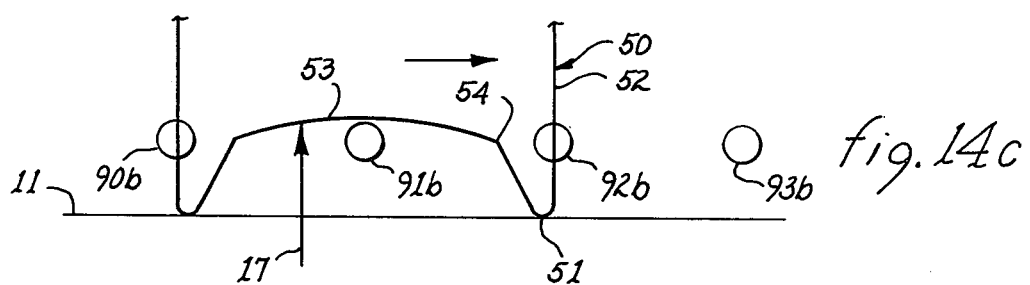
Figure 14D:
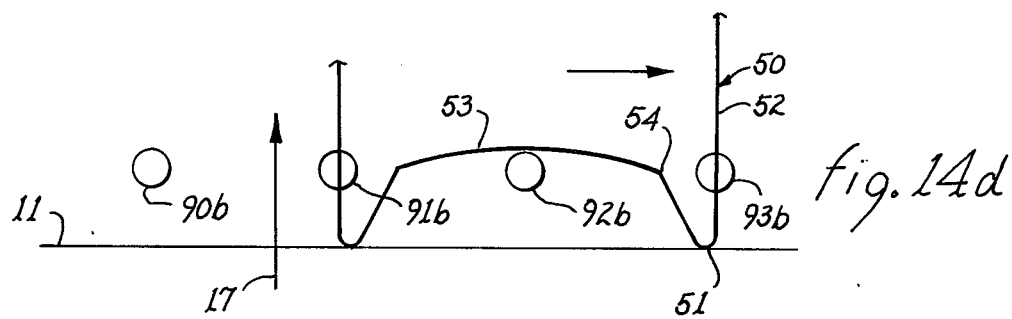

The sequence of operation of the sensors illustrated in FIG. 13 will be discussed with respect to FIGS. 14a, 14b, 14c and 14d. On translation of can 50 along conveyer belt 11 toward beam 17, the leading edge of the can, cylindrical surface 52, will intercept sensor 90. The signal generated by the sensor is employed to clear the attendant circuitry and initiate the start of a new cycle. As can 50 continues its translational movement, beam 17 will impinge upon ridge 51 and energize detector 71 of the detector array, as depicted in FIG. 9. Further translation of the can will cause interception of the signal intermediate the transmitter and receiver of sensor 91. The physical displacement along the direction of travel between sensor 91 and beam 17 is equal to or commensurate with the physical displacement between cylindrical surface 52 and annular junction 54. On interruption of sensor 91, a signal is generated indicative of determination of the counter sink ("a") and detector 74 (see FIG. 10) is so identified. The subsequently energized detectors within the detector array are thereby representative solely of the curvature of bottom area 53.

Sensor 92 is positioned with respect to beam 17 such that the area traversed by the beam along bottom area 53 from annular junction 54 represents the area of intended inspection. The interruption of sensor 92 generates a signal identifying the then energized detector of detector array 24 as the terminal detector to provide an indication of the path illuminated upon bottom area 53 which is to be analyzed and compared within the circuitry.

Continuing translation of can 50 will ultimately result in interruption of the beam intermediate transmitter 93a and receiver 93b of sensor 93. Interruption of this sensor generates a signal to the circuitry to begin the analysis and comparison functions and generate an output signal representative of whether the bottom area of the can passed or failed the inspection.

If presently available circuitry, whether analog, digital or hybrid, is employed, the speed of signal generation, analysis and comparison is extremely high. In fact, the time period required for these purposes is only a small fraction of the time required to translate the can under inspection past beam 17. Therefore, it becomes evident that the inspection system of the present invention is completely independent of the speed of conveyer 11 and will accommodate any presently known speed for such conveyers.

It may also be pointed out that by adjustably mounting sensors 90, 91, 92 and 93, any part of any can, regardless of configuration, can be inspected over an area of interest regardless of the displacement of the area of interest from a reference plane.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

We claim:

1. Apparatus for inspecting and comparing surface features of each of a plurality of containers transported by a conveyer with predetermined surface features of a standard container to determine whether the inspected container is within an allowable tolerance of the standard container, said apparatus comprising in combination:

(a) means for producing and directing at least one beam of radiant energy along a fixed axis to irradiate a surface area of each container being inspected as the conveyer transports the container past the beam;

(b) a plurality of energizable detector means for detecting radiant energy scattered from segments of the irradiated surface area;

(c) means for transmitting the radiant energy scattered by a segment of the irradiated surface area to a predeterminable one of said plurality of detector means if the irradiated segment is commensurate in configuration with an equivalent segment of the standard container and to another of said plurality of detector means if the irradiated segment is not commensurate in configuration with an equivalent segment of the standard container;

(d) a first sensor responsive to the location with respect to the beam of a first predetermined characteristic of the container to be inspected as the container is conveyed by the conveyer past the beam for providing a first signal coincident in time with the expected energization of one specific detector of the plurality of detector means upon irradiation of a specific segment of the irradiated surface area;

(e) a second sensor responsive to the location with respect to the beam of a second predetermined characteristic of the container to be inspected as the container is conveyed by the conveyer past the beam for providing a second signal coincident in time with the expected energization of another specific detector of the plurality of detector means upon irradiation of another specific segment of the irradiated surface area;

(f) means for generating an output signal reflective of the degree of correlation between the detectors of said plurality of detector means actually energized coincident with said first and second signals and the specific detectors of said plurality of detectors expected to be energized upon irradiation of specific segments of the irradiated surface area;

whereby, the output signal is indicative of the degree of tolerance of the inspected container with the standard container.

2. The apparatus as set forth in claim 1 including a third sensor responsive to translation of the container to be inspected past the beam for providing a third input signal to said generating means to initiate generation of the output signal.

3. The apparatus as set forth in claim 2 further including a further sensor responsive to translation of the container to be inspected past the beam for providing a further input signal to said generating means to terminate generation of the output signal.

4. The apparatus as set forth in claim 3 wherein said producing and directing means includes means for directing the beam to one end of the container under inspection.

5. The apparatus as set forth in claim 4 wherein said directing means directs the beam to the bottom of the container under inspection.

6. The apparatus as set forth in claim 1 including a further sensor responsive to translation of the container to be inspected past the beam for providing a further input signal to said generating means to terminate generation of the output signal.

7. The apparatus as set forth in claim 6 wherein said producing and directing means includes means for directing the beam to one end of the container under inspection.

8. The apparatus as set forth in claim 7 wherein said directing means directs the beam to the bottom of the container under inspection.

9. A method for inspecting and comparing surface features of each of a plurality of containers transported by a conveyer with predetermined surface features of a standard container to determine whether the inspected container is within an allowable tolerance of the standard container, said method comprising the steps of:

(a) producing and directing at least one beam of radiant energy to irradiate a surface area of each container being inspected as the conveyer transports the container past the beam;

(b) detecting with a plurality of energizable detectors the radiant energy scattered from segments of the irradiated surface area;

(c) transmitting the radiant energy scattered by a segment of the irradiated surface area to a predeterminable one of the plurality of detectors if the irradiated segment is commensurate in configuration with an equivalent segment of the standard container and to another of the plurality of detectors if the irradiated segment is not commensurate in configuration with an equivalent segment of the standard container;

(d) providing a first signal coincident in time with the expected energization of one specific detector of the plurality of detectors by irradiation of a specific segment of the irradiated surface area in response to the location with respect to the beam of a first predetermined characteristic of the container to be inspected as the container is conveyed by the conveyer past the beam;

(e) providing a second signal coincident in time with the expected energization of another specific detector of the plurality of detectors by irradiation of another specific segment of the irradiated surface area in response to the location with respect to the beam of a second predetermined characteristic of the container to be inspected as the container is conveyed by the conveyer past the beam;

(f) generating an output signal reflective of the degree of correlation between the detectors of the plurality of detectors actually energized coincident with the first and second signals and the specific detectors of the plurality of detectors expected to be energized upon irradiation of specific segments of the irradiated surface area;

whereby, the output signal indicates the degree of tolerance of the inspected container with the standard container.

10. The method as set forth in claim 9 including the step of providing a third input signal in response to translation of the container to be inspected past the beam to initiate generation of the output signal.

11. The method as set forth in claim 10 including the step of providing a further input signal in response to translation of the container to be inspected past the beam to terminate generation of the output signal.

12. The method as set forth in claim 11 including the step of directing at least one beam of radiant energy to irradiate one end of the container under inspection.

13. The method as set forth in claim 12 wherein said step of directing includes the step of irradiating the bottom of the container under inspection.

14. The method as set forth in claim 9 including the step of providing a further input signal in response to translation of the container to be inspected past the beam to terminate generation of the output signal.

15. The method as set forth in claim 14 including the step of directing at least one beam of radiant energy to irradiate one end of the container under inspection.

16. The method as set forth in claim 15 wherein said step of directing includes the step of irradiating the bottom of the container under inspection.

* * * * *